United States Patent

Cornell

[11] Patent Number: 6,044,287
[45] Date of Patent: Mar. 28, 2000

[54] MEDICAL ELECTRODE WITH EDGE DEADENING

[75] Inventor: George Cornell, Ramona, Calif.

[73] Assignee: Axelgaard Manufacturing Co., Ltd., Fallbrook, Calif.

[21] Appl. No.: 09/114,372

[22] Filed: Jul. 14, 1998

[51] Int. Cl.[7] .................................. A61B 5/04; A61N 1/04
[52] U.S. Cl. ...................... 600/391; 600/392; 607/149; 607/152; 29/825
[58] Field of Search ...................................... 600/391, 392, 600/395–397; 607/149, 152, 153; 29/825

[56] References Cited

U.S. PATENT DOCUMENTS

| | | | |
|---|---|---|---|
| 4,736,752 | 4/1988 | Munck et al. | 607/152 |
| 4,979,517 | 12/1990 | Grossman et al. | 607/152 |
| 5,133,355 | 7/1992 | Strand et al. | 600/392 |
| 5,571,165 | 11/1996 | Ferrari | 607/152 |

*Primary Examiner*—Lee Cohen
*Attorney, Agent, or Firm*—Walter A. Hackler

[57] ABSTRACT

A medical electrode includes a conductive flexible member with a non-conductive flexible sheet disposed on a top side thereof. A connector is provided for establishing electrical contact between the conductive flexible member and an external electrical device and a conductive adhesive adhered to a bottom side of the conductive flexible member provides electrical conductivity to a patient's skin. The conductive adhesive includes a contact surface for application to a patient's skin and an edge perimeter subtending the contact surface and the conductive flexible member. A non-conductive coating is disposed on the edge perimeter of the conductive adhesive for providing an environmental and electrical barrier.

17 Claims, 1 Drawing Sheet

MEDICAL ELECTRODE WITH EDGE DEADENING

The present invention generally relates to biomedical electrodes and, more particularly, electrodes suitable for transcutaneous, nerve and/or muscle stimulation as well as biological signal recording.

Efficient medical electrodes must provide an appropriate conductive interface between the electrode and a patient's skin. This appropriate conductive interface includes even electrical coupling to the patient's skin over an entire surface of the electrode.

Because of the curvaceous nature of the human body, it is necessary that medical electrodes for use thereon must not only be flexible, for conformation to a patient's skin contours, but also to accommodate a movement of the patient's skin.

In order to provide uniform electrical coupling, heretofore developed electrodes have utilized conductive fabrics, foils and combination with a conductive adhesive in order to uniformly couple electrical signals to and/or from an electrical lead wire, or connector.

A common prior art problem with medical electrodes using a conductive adhesive is the leakage of electrical current from edges of the conductive adhesive, or gel, which is known in the art as edge biting. In addition, exposed adhesive, or gel, has a tendency to dry upon exposure to air and, in addition, entry of foreign material to the gel is possible because of the adhesive nature thereof.

The present invention addresses these problems with prior art electrodes.

SUMMARY OF THE INVENTION

A medical electrode in accordance with the present invention generally includes a conductive flexible member having a top side and a bottom side with a non-conductive flexible sheet covering the conductive flexible member top side.

A connector provides means for establishing electrical contact between the conductive flexible member and an external electrical device which may be, for example, a recording system, or a pulse generation system for therapy stimulation, such as transcutaneous electrical nerve stimulation.

A conductive adhesive adhered to the conductive flexible member bottom side provides electrical conductivity to a patient's skin. The conductive adhesive has a contact surface for application to the patient's skin and an edge perimeter subtending both the contact surface and the conductive flexible member.

Importantly, a non-conductive coating disposed on the edge perimeter of the conductive adhesive provides a means for reducing the electrical current leakage from the edge perimeter and, in addition, provides a barrier to air and foreign material. The non-conductive coating is flexible in order to accommodate flexure of the conductive flexible member, non-conductive flexible sheet and the conductive adhesive.

In addition, because the coated adhesive edge perimeter is no longer tacky, there is less likelihood that an edge of the electrode may be lifted due to contact with a patient's clothing, for example.

More particularly, the coating means may comprise a particulate material, such as, for example, glass spheres. Still more particularly the glass spheres may have a diameter of between about 0.001 inches (0.004 mm) to about 0.015 inches (0.06 mm).

Still more particularly, in accordance with the present invention, the conductive adhesive perimeter edge may have a diameter greater than a diameter of the conductive flexible member. This ensures more uniform coupling of the electrical current to a patient's skin by reducing "drop off" caused by edge effects of the conductive member.

Also, in order to reduce edge effects and provide more uniform coupling, the conductive adhesive edge perimeter may subtend both the electrical conductive member and the non-conductive flexible cover sheet.

In addition, at least some of the particulate media may be embedded into the conductive adhesive edge perimeter.

Thus, the particulate media in accordance with the present invention provides an environmental and electrical barrier having the advantages hereinabove recited.

Accordingly, a method in accordance with the present invention of making an medical electrode includes the steps of disposing a conductive adhesive onto a release layer, disposing a conductive flexible member onto the conductive adhesive. The conductive flexible member is disposed on the conductive adhesive so as to form an edge perimeter of the conductive adhesive subtending the release layer and the conductive flexible member. A non-conductive flexible sheet is disposed over the conductive flexible member and the edge perimeter is coated with a non-conductive particulate media as hereinabove described.

BRIEF DESCRIPTION OF THE DRAWINGS

The advantages and features of the present invention will be better understood by the following description and drawings in which.

DETAILED DESCRIPTION OF THE DRAWINGS

Figure 1:
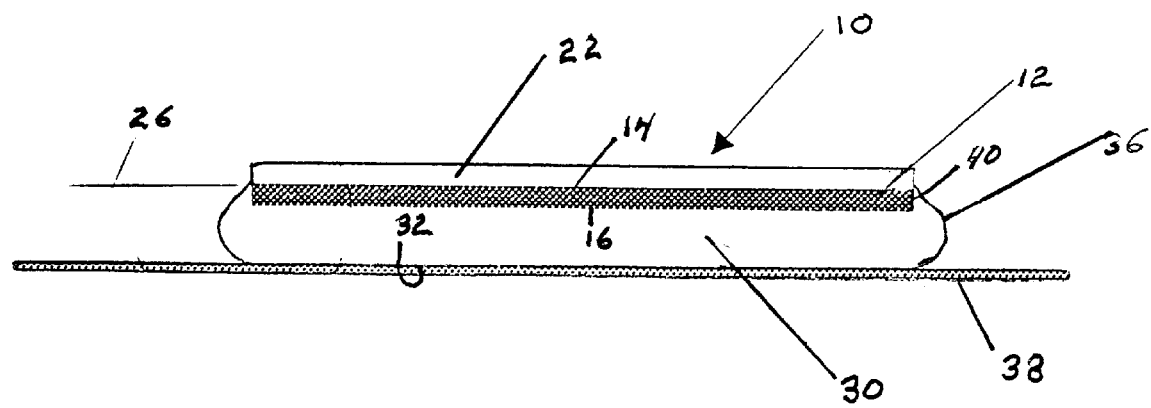
FIG. 1 is a cross section representation of an electrode made in accordance with the present invention generally showing a conductive member, a non-conductive cover sheet and a conductive adhesive having an edge perimeter with a coating thereon.

With reference to FIG. 1, there is shown a medical electrode 10 made in accordance with the present invention, which generally includes a conductive flexible member 12 having a top side 14 and bottom side 16. This conductive member may be made of any suitable type, as for example, a conductive fabric as set forth in U.S. Pat. Nos. 4,722,354, 4,708,149, 4,819,328, 4,867,167 to Axelgaard, or a conductive coating as set forth in U.S. Pat. No. 4,736,752 to Munck et al. All of these patents are to be incorporated herewith by this reference thereto for the purpose of teaching the types of conductive members which are suitable for use in the present invention.

A non-conductive flexible sheet 22 covers the flexible member topside 14 in a conventional manner which is also taught in the hereinabove referenced U.S. patents which are also incorporated for the purpose of teaching the types of non-conductive flexible sheets useful in accordance with the present invention.

A connector 26 provides a means for establishing electrical contact between the conductive flexible member 12 and an external electrical device (not shown). Again, this connector, or lead wire, is taught in the hereinabove referenced U.S. patents.

A conductive adhesive means 30 provides electrical conductivity to a patient's skin (not shown) with the conductive adhesive means 30 adhered to the conductive flexible member bottom side 16 and having a contact surface 32 for application to the patient's skin (not shown) and an edge of perimeter 36 subtending the contact surface 32 and the flexible conductive member 12 before application to a patient (not shown). The conductive adhesive means 30 is disposed on a release layer 38 which is well known in the art.

Suitable conductive adhesives for use in the present invention are taught in U.S. patent application Ser. No. 08/603,635 entitled, "MEDICAL ELECTRODE", filed Feb. 20, 1996, now U.S. Pat. No. 5,868,136. This application is to be incorporated herewith for teaching the types of conductive adhesives suitable for use with the present invention.

Preferably, the adhesive edge perimeter 36 has a diameter greater than a diameter of the conductive member 12, as shown in FIG. 1, as a convex protrusion of the conductive adhesive means 32 past an edge 40 of the conductive member 12. As hereinabove noted, this configuration enables more uniform distribution with less falloff of the current distribution at the edge 40 of the conductive member. In addition, the edge perimeter 36 preferably subtends both the non-conductive sheet 22 and the conductive member 12 as more clearly shown in FIG. 2.

Heretofore, the electrodes generally using the design concept of the present invention resulted in inherent problems with areas or edges of unwanted stickiness. These areas of adhesion create handling problems for manufacturing, product packaging and the end user, by sticking to areas other than desired. Other problems associated with prior art electrodes have been hereinabove discussed.

The present invention solves this problem by neutralizing the stickiness of the edge perimeter 36 through the use of a particulate media 44 which provides a non-conductive coating means for reducing electrical current leakage from the edge perimeter 36 and for providing a barrier to air and foreign material.

The particulate media may be of any suitable non-conductive particulates, but preferably is comprised of glass spheres 44. Such spheres preferably have a diameter in the order of 0.001 inches to about 0.15 inches which enables a free pouring particulate media which is immune to moisture, resistant to static charge build-up, dielectric, easy to acquire and inexpensive.

Figure 2:
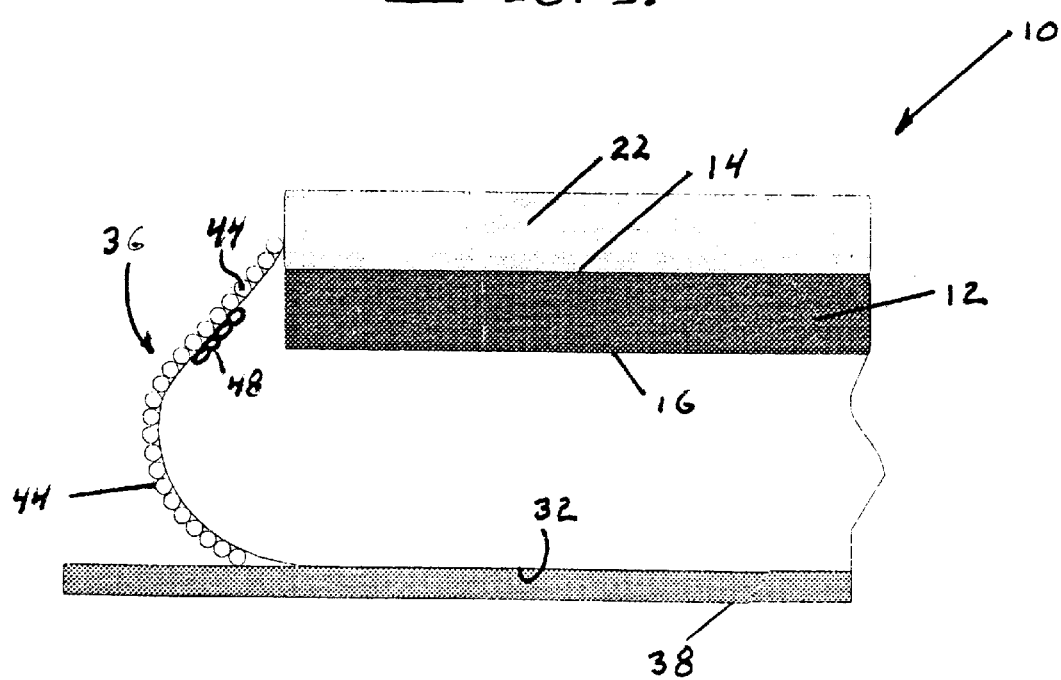
FIG. 2 is an enlargement of the perimeter of the electrode shown in FIG. 1, more clearly illustrating the coating on the conductive adhesive edge perimeter.

Application of these spheres 44 may be made by a simple contact of the conductive adhesive edge perimeter 36 therewith or by forcing the spheres 44 into the adhesive 30 in order to embed some spheres 48 as represented in FIG. 2.

When applied to the edge perimeter 36, these spheres 44, 48 become a coating which is flexible and can accommodate flexure of the conductive flexible member 12, the non-conductive flexible sheet 22 and the conductive adhesive 30.

Prior to use as hereinabove noted, the conductive adhesive 30 is applied to a release layer 38 which is removed before application of the medical electrode 10 to a patient's skin (not shown).

Accordingly, the coating of spheres 44 provides an environmental and electrical barrier which is disposed on the edge perimeter 36 which, in addition to reducing any unwanted current leakage or "edge bite", reduces the exposure of the conductive adhesive 30 to air and accordingly prevents drying thereof. Thus, the edge perimeter 36 is no longer tacky and accordingly does not attract any foreign material, nor enable the unwanted lifting of the medical electrode from a patient's skin by inadvertent contact with clothing, or the like.

The method of the present invention includes the assembly of the hereinabove referenced components and the application of the coating 44 as hereinabove discussed.

Although there has been described hereinabove a specific arrangement of a medical electrode in accordance with the present invention for the purpose of illustrating the manner in which the invention may be used to advantage, it should be appreciated that the invention is not limited thereto. Accordingly, any and all variations and modifications which may occur to those skilled in the art are to be considered to be within the scope and spirit of the invention as defined in the appended claims.

What is claimed is:

1. A medical electrode comprising:
   a conductive flexible member having a top side and a bottom side;
   a non-conductive flexible sheet covering the conductive flexible member top side;
   connector means for establishing electrical contact between said conductive flexible member and an external electrical device;
   conductive adhesive means, adhered to the conductive flexible member bottom side, for providing electrical conductivity to a patient's skin, said conductive adhesive means having a contact surface for application to the patient's skin and an edge perimeter subtending the contact surface and said conductive flexible member; and
   non-conductive coating means, disposed on the edge perimeter of said conductive adhesive means, for reducing electrical current leakage from the edge perimeter and for providing a barrier to air and foreign material, said non-conductive coating means being flexible in order to accommodate flexure of the conductive flexible member, non-conductive flexible sheet and said conductive adhesive means, said non-conductive coating means comprising a particulate media.

2. The medical electrode according to claim 1 wherein said particulate media comprises glass spheres.

3. The medical electrode according to claim 2 wherein said glass spheres have a diameter of between about 0.001 inches to about 0.015 inches.

4. The medical electrode according to claim 1 wherein the conductive adhesive means edge perimeter has a diameter greater than a diameter of said conductive flexible member.

5. The medical electrode according to claim 4 wherein the conductive adhesive means edge perimeter further subtends said non-conductive flexible sheet.

6. The medical electrode according to claim 5 wherein said particulate media comprises glass spheres.

7. The medical electrode according to claim 6 wherein said glass spheres have a diameter of between about 0.001 inches to about 0.015 inches.

8. The medical electrode according to claim 1 wherein at least some of the particulate media is embedded into the conductive adhesive means edge perimeter.

9. The medical electrode according to claim 8 wherein said particulate media comprises glass spheres.

10. The medical electrode according to claim 9 wherein said glass spheres have a diameter of between about 0.001 inches to about 0.015 inches.

11. A medical electrode comprising:
    a conductive flexible member having a top side and a bottom side;
    a non-conductive flexible sheet covering the conductive flexible member top side;
    connector means for establishing electrical contact between said conductive flexible member and an external electrical device;

conductive adhesive means, adhered to the conductive flexible member bottom side, for providing electrical conductivity to a patient's skin, said conductive adhesive means having a contact surface for application to the patient's skin and an edge perimeter subtending the contact surface and said conductive flexible member; and an environmental and electrical barrier disposed on the edge perimeter of said conductive adhesive means, the barrier being flexible in order to accommodate flexure of the conductive flexible member, non-conductive flexible sheet and said conductive adhesive means, the barrier comprising a particulate media.

12. The medical electrode according to claim 11 wherein said particulate media comprises glass spheres.

13. The medical electrode according to claim 12 wherein said glass spheres have a diameter of between about 0.001 inches to about 0.015 inches.

14. The medical electrode according to claim 11 wherein the conductive adhesive means edge perimeter has a diameter greater than a diameter of said conductive flexible member.

15. The medical electrode according to claim 14 wherein the conductive adhesive means edge perimeter further subtends said non-conductive flexible sheet.

16. The medical electrode according to claim 11 wherein at least some of the particulate media is embedded into the conductive adhesive means edge perimeter.

17. A method of making a medical electrode comprising the steps of:

disposing a conductive adhesive onto a release layer;

disposing a conductive flexible member onto the conductive adhesive, said conductive flexible member being disposed so as to form an edge perimeter of conductive adhesive subtending said conductive flexible member;

disposing a non-conductive flexible sheet over said conductive flexible member; and coating said edge perimeter with non-conductive particulates.

* * * * *